(12) United States Patent
Chen et al.

(10) Patent No.: US 6,407,208 B1
(45) Date of Patent: Jun. 18, 2002

(54) CHIMERIC PROTEINS WITH A CELLULOSE BINDING DOMAIN

(76) Inventors: David Chanhan Chen, No. 8, Lane 173, Ta-Kuang St., 17 Lin, Kou-Chien Li, Nan-Tun District; Nien-Tai Hu, No. 14-13, Sec. 1, Hsiang-Shang Rd., 2 Lin, Ching-Lung Li, West District, both of Taichung; Yun-Ju Chen, 11F-1, No. 182, Sung-Chiang Rd., 7 Lin, Chung-Chi Li, Chung-Shan District, Taipei; Tzong-Hsiung Hseu, No. 23, Chen-Fu St., 3 Lin, Chao-Yang Li, Taoyuan, all of (TW)

( * ) Notice: Subject to any disclaimer, the term of this patent is extended or adjusted under 35 U.S.C. 154(b) by 0 days.

(21) Appl. No.: 09/166,966

(22) Filed: Oct. 6, 1998

(30) Foreign Application Priority Data

Oct. 8, 1997 (TW) .......................... 86114750

(51) Int. Cl.[7] .......................... C07K 14/00; C07K 1/00; C12N 9/00
(52) U.S. Cl. ...................... 530/350; 435/183; 435/209; 435/440; 536/23.4; 530/324
(58) Field of Search ................... 435/183, 209, 435/440; 536/23.4; 530/350

(56) References Cited

U.S. PATENT DOCUMENTS

| | | |
|---|---|---|
| 5,137,819 A | 8/1992 | Kilburn |
| 5,202,247 A | 4/1993 | Kilburn |
| 5,340,731 A | 8/1994 | Kilburn |
| 5,496,934 A | 3/1996 | Shoseyov |
| 5,874,308 A * | 2/1999 | Kilburn et al. .............. 435/395 |

OTHER PUBLICATIONS

Wey et al. Molecular Cloning and Sequence Analysis of the Cellobiohydrolase I Gene from Trichoderma koningii G–39, Curr. Micro. 28: 31–39, 1994.*
LaVallie et al. A Thioredoxin Gene Fusion Expression System That Circumvents Inclusion Body Formation in the E. coli Cytoplasm, Bio/Technology 11: 187–193, Feb. 1993.*
Shoseyov, Primary Sequence Analysis of Clostridium Cellulovorans Cellulose Binding Protein A, Apr. 1992.
Wierzba, Production and Properties of a Bifunctional Fusion Protein that Mediates Attachment of Vero Cells to Cellulosic Matrices, Feb. 1995.
Linder, Markus, et al., *The difference in affinity between two fungal cellulose–binding domain dominated by a single amino acid substitution*, FEBS Letters 372, p. 96–98 (1995).

* cited by examiner

*Primary Examiner*—Elizabeth Slobodyansky
*Assistant Examiner*—Richard Hutson
(74) *Attorney, Agent, or Firm*—Fei-Fei Chao; Venable, Baetjer, Howard & Civiletti, LLP

(57) ABSTRACT

Chimeric proteins containing a cellulose binding domain (CBD) situated between two independent desired proteins of different lengths can be contemplated for use in a wide range of applications. In addition to its affinity to cellulose due to the presence of the CBD, various properties can be adopted to the chimeric protein by means of introducing the desired proteins upstream and downstream of the CBD. For example, a chimeric protein is produced in *Escherichia coli* in large quantities by joining a thioredoxin, a CBD and a short peptide composed of 3 amino acid (i.e., Arginine-Glutamate-Asparate). This chimeric protein can be further purified in simple steps and added to cell culture to enhance cell attachment to a surface made up of cellulose.

3 Claims, 8 Drawing Sheets

```
code      5      10      15      20      25      30      35
CBD   TQSHY GQCGG IGYSG PTVCA SGTTC QVLNP YYSQC L
(from CBHI)
            |_____|
                disulfide        |_____|
                  bond              disulfide
                                      bond
```

Fig. 1

```
         T7 promoter
5'--  TAATACGA  CTCACTATAG  GGGAATTGTG  AGCGGATAAC  AATTCCCCTC
3'--  ATTATGCT  GAGTCATATC  CCCTTAACAC  TCGCCTATTG  TTAAGGGGAG 5'--TAGAAATAAT   TTTGTTTAAC  TTTAAGAAGG  AGATATACAT  ATG  AGC
3'--ATCTTTATTA   AAACAAATTG  AAATTCTTCC  TCTATATGTA  TAC  TCG
a.a.                                                 M    S Thioredoxin
5'--315bp      CTG  GCC  GGT  TCT  GGT  TCT  GGC  CAT  ATG  CAC  CAT
3'--           GAC  CGG  CCA  AGA  CCA  AGA  CCG  GTA  TAC  GTG  GTA
a.a            L    A    G    S    G    S    G    H    M    H    H 5'--CAT  CAT  CAT  CAT  TCT  TCT  GGT  CTG  GTG  CCA  CGC  GGT  TCT
3'--GTA  GTA  GTA  GTA  AGA  AGA  CCA  GAC  CAC  GGT  GCG  CCA  AGA
a.a. H   H    H    H    S    S    G    L    V    P    R    G    S 5'--GGT  ATG  AAA  GAA  ACC  GCT  GCT  GCT  AAA  TTC  GAA  CGC  CAG
3'--CCA  TAC  TTT  CTT  TGG  CGA  CGA  CGA  TTT  AAG  CTT  GCG  GTC
a.a. G   M    K    E    T    A    A    A    K    F    E    R    Q NcoI
5'--AAG  GCC  ATG  G
3'--TTC  CGG  TAC  C
a.a. K   A    M
```

Fig. 2

Oligonucleotide

```
            NcoI
A.  5'- CT  TCC ATG GCT ACC CAG TCT CAC TGG GGC CAG TGC G-3'
            NheI
B.  5'- TCA GCT AGC GCT GTC ACC ACG ACC AGT TGG AGT AGT TGG
        CAG GCA CTG A-3'
```

Fig. 3

```
5'--CT TCC ATG GCT ACC CAG TCT CAC TGG GGC CAG TGC GGC GGT ATT GCC TAC AGC GGC CCC
3'--GA AGG TAC CGA TGG GTC AGA GTG ACC CCG GTC ACG CCG CCA TAA CGG ATG TCG CCG GGG
A.A.--      M   A   T   Q   S   H   W   G   Q   C   G   G   I   A   Y   S   G   P    59
                                                                                       P

5'--ACG GTC TGC GCC AGC GGC ACA ACT TGC CAG GTC CTG AAC CCT TAC TAC TCT CAG TGC CTG
3'--TGC CAG ACG CGG TCG CCG TGT TGA ACG GTC CAG GAC TTG GGA ATG ATG AGA GTC ACG GAC
A.A.   T   V   C   A   S   G   T   T   C   Q   V   L   N   P   Y   Y   S   Q   C   L  119

5'--CCA ACT ACT CCA ACT GGT CGT GGT GAC AGC GCT AGC TGA ACT
3'--GGT TGA TGA GGT TGA CCA GCA CCA CTG TCG CGA TCG ACT
A.A.   P   T   T   P   T   G   R   G   D   S   A   S   ---                             158
```

Fig. 4

A
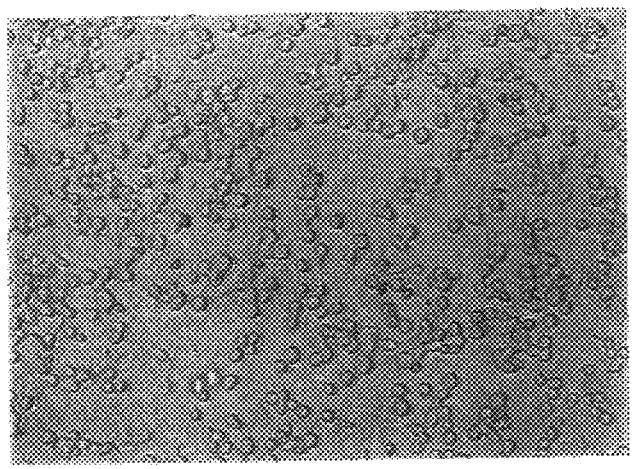
B
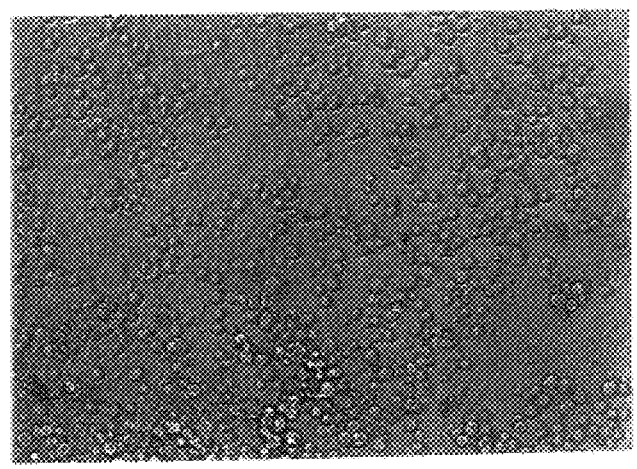
C
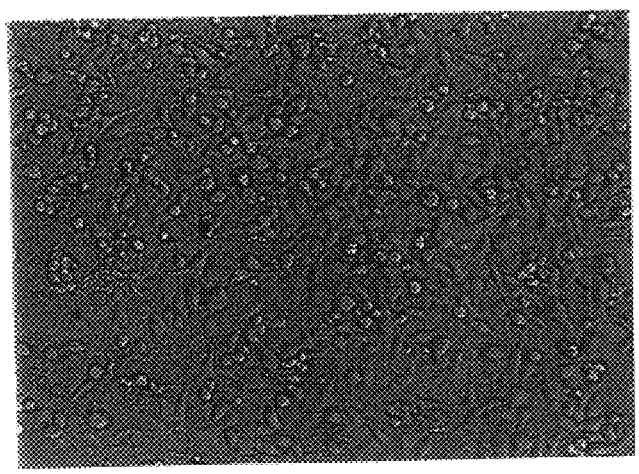
Fig. 8

CHIMERIC PROTEINS WITH A CELLULOSE BINDING DOMAIN

A. FIELD OF THE INVENTION

This invention relates to multi-functional chimeric proteins and the method of making these chimeric proteins by genetic recombinant techniques. The chimeric proteins of the present invention contain a cellulose binding domain.

B. BACKGROUND OF THE INVENTION

Serum is a necessary supplement in an anchorage cell culture. It is used to help culture cells attach onto the culture plates as well as to enhance cell-growth. Serum is also the most expensive component in a culture medium primarily due to limited sources. However, the qualities of serum from different sources vary highly, which may directly or indirectly contribute to the unstable physiologic property of cells. Therefore, it is necessary to develop an economic substitute for serum while still enabling the stable physiologic property of cells.

Chimeric proteins, i.e., the proteins containing both a functional domain (catalytic or otherwise) and a binding domain, have been used in various ways, especially in protein purification. For example, the chimeric protein composed of a desired protein fused with the c-terminal of a glutathione S-transferase is used widely in bio-technologic related fields, wherein the fused protein can be purified by a glutathione-Sepharose column. By means of the association between the binding domain of the chimeric protein and the substrate of the binding domain which is immobilized on a solid matrix such as beads, resins, plates, etc, the desired products can be conveniently purified.

Cellulose, a major component of the cellular walls of plants, is a continuous linear glucose β-1,4 linkage polysaccharide which is readily available in the nature. Cellulase is a hydrolase of cellulose, wherein the cellulase can digest the cellulose by cleaving the β-1,4 glycosidic bonds of cellulose. It is well known that the sequence encoding the cellulase comprises a cellulose-binding domain (CBD) allowing cellulose to bind to cellulose and subsequently cleave the β-1,4 glycosidic bonds of cellulose. It is disclosed in U.S. Pat. No. 5,496,934 that the CBD has a high affinity for crystalline cellulose having a $K_d$ ranging from 1.5 to about 0.8, preferably from about 1.4 to about 0.8, and the chimeric protein comprising CBD and a second protein retains the avid binding capacity of the CBD to cellulose. By means of the binding affinity between the cellulose-binding domain and the cellulose, the cellulase can be immobilized on the matrix coated with cellulose by the binding domain thereof. In addition, the cellulose prices are 100–500 fold lower than those of glutathione-Sepharose, making cellulose an attractive, inexpensive matrix that can be used safely in food and pharmaceutical industries. Therefore, it is highly beneficial to develop a cheap purification system by joining the desired protein with a cellulose binding domain, or to create a substitute for serum by joining an anchorage enhancer and a growth factor with a cellulose binding domain.

Dead plants and fallen leaves in nature are digested by microorganisms with the ability of cellulose digestion. The microorganisms with the ability of cellulose digestion comprise eukaryotes such as eumycetes, and prokaryotes such as bacteria. The microorganisms described above can synthesize cellulase to digest the cellulose into small molecules, which can be further digested by other saccharide hydrolases. Gene cloning and sequencing results (Shoseyov et al., *Proc. Natl. Acad. Sci. USA*, 89:3483–3487, 1992) have demonstrated that the cellulase contains two independent functional regions: a catalytic domain with cellulase property, and a cellulose binding domain (CBD). Also, the biochemistry test results demonstrate that these two domains are functioned independently.

Chimeric proteins with a cellulose binding protein have been disclosed in several U.S. patents and literature. For example, U.S. Pat. No. 5,202,247 discloses a cellulose binding fusion protein having a substrate binding region of cellulose; U.S. Pat. No. 5,137,819 discloses cellulose binding fusion proteins for immobilization and purification of polypeptides; U.S. Pat. No. 5,340,731 describes a method of preparing a β-1,4-glycan matrix containing a bound fusion protein; and U.S. Pat. No. 5,496,934 discloses nucleic acids encoding a cellulose binding domain. Moreover, Wierzba et al., *Biotechnol. Bioeng.* 47:147–154, 1995, discloses a chimeric protein which consists of the c-terminal binding domain of cellulase from bacteria and an amino acid sequence with the ability of cell-attachment. The chimeric protein can enhance cells anchorage on the matrix coated with cellulose.

The cellulose binding domain of the above patents and literature is primarily obtained from bacteria, wherein the cellulose binding domain located at the N-terminal of cellulase and the C-terminal catalytic domain are isolated from a proline- and threinine-rich amino acid sequence.

However, the cellulose binding domain of eumycetes is much shorter than that of bacteria, and the structure of the cellulose binding domain of eumycetes is much denser than that of bacteria.

The present invention involves the production of a recombinant chimeric protein which contains a cellulose binding domain from eumycetes. This chimeric protein not only allows the insertion of long amino acid sequences, but also is capable of allowing insertion of short amino acid sequence (e.g., three amino acid sequences). The chimeric protein is obtained by joining functional amino acid sequences on the N- and C-terminals of a cellulose binding domain. For example, one terminal of the cellulase binding domain can be joined to a cell-attachment enhancer, and the other terminal of the cellulase can be joined to a growth factor, thereby producing a chimeric protein that can enhance both the cells ability to anchor on the matrix coated with cellulose and cell growth. One difficulty that must be overcome, however, is how to correctly link the two disulfide bonds within the cellulose binding domain. Another difficulty is how the disulfide binds can be formed correctly and be exposed on the surface of the chimeric protein to retain the cellulose binding ability when the N-terminal cellulose binding domain is located between two amino acid sequences.

SUMMARY OF THE INVENTION

The invention features a multi-functional chimeric protein produced by genetic recombinant techniques, wherein two exogenous bifunctional amino acid sequences are respectively joined at the C-terminal and the N-terminal of the cellulose binding domain of cellulase obtained from *Trichoderma konigii* G39 (cellulobiohydrolase I, CEH I) to generate a recombinant protein. In addition to the cellulose binding ability, the function of the chimeric protein is determined by the sequences joined at the C-terminal and the N-terminal. By means of the cellulose binding ability of a cellulose binding domain (CBD), the desired protein joined with the CBD can be immobilized on the matrix, applied to cell cultures, as well as used for antibody or antigen detection and other medically related industries. The desired protein can be selected from the group consisting of thioredoxin, an Arginine-Glutamate-Asparate (RGD) tripeptide, Protein A, Protein G, streptavidin, avidin, Taq polymerase, non-Taq polymerase, alkaline phosphatase, RNase, DNase, restriction enzymes, peroxidases, glucanases, chitinases, beta and alpha glucosidases, beta and alpha glucoronidase, amylases, transferases, beta-lactamase, non-beta lactamase antibiotic modifying and degrading enzymes, luciferase, esterases, lipases, proteases, bacteriocines, antibiotics, enzyme inhibitors, growth factors, hormones, receptors, antigens, membrane proteins, nuclear proteins, transcriptional and translational factors and nucleic acid modifying enzymes.

This invention also provides a method of overexpressing a CBD fused product, wherein the method comprises the following steps: (a) providing a first DNA fragment comprising the coding sequence of the CBD; (b) joining a second DNA sequence and a third DNA sequence encoding two desired proteins to a 5'-end and a 3'-end of said first DNA fragment to form a recombinant DNA molecule encoding the CBD fused product; (c) cloning the recombinant DNA molecule in a vector with a selected marker to construct an expression vector comprising the recombinant DNA molecule encoding the CBD fused product; (d) transferring the expression vector into a cell to form a transformed cell; (e) overexpressing the CBD fused product in the transformed cell. The recombinant DNA molecule is preferably inserted into the vector downstream from a promoter site. The perferable promoter is T7.

The cellulose binding domain described above can be isolated from microorganisms such as the cellulobiohydrolase I of *Trichoderma konigii* G39 (CCRC 930014). Moreover, the first DNA fragment which encodes the cellulose binding domain can be modified by replacing the code encoding the fifth amino acid residue of the cellulose binding domain from tyrosine to tryptophan. The desired protein can be selected from the group consisting of thioredoxin, an Arginine-Glutamate-Asparate (RGD) tripeptide, Protein A, Protein G, streptavidin, avidin, Taq polymerase, non-Taq polymerase, alkaline phosphatase, RNase, DNase, restriction enzymes, peroxidases, glucanases, chitinases, beta and alpha glucosidases, beta and alpha glucoronidase, amylases, transferases, beta-lactamase, non-beta lactamase antibiotic modifying and degrading enzymes, luciferase, esterases, lipases, proteases, bacteriocins, antibiotics, enzyme inhibitors, growth factors, hormones, receptors, antigens, membrane proteins, nuclear proteins, transcriptional and translational factors and nucleic acid modifying enzymes. The cell for transformation can be either a prokaryote or a eukaryote. In addition, the method further comprises a step to purify the CBD fused product by an ion-exchange liquid chromatography such as an anion-exchange resin DE52.

Other features or advantages of the present invention will be apparent from the following drawings and detailed description of the example, and also the claims.

II. BRIEF DESCRIPTION OF THE DRAWINGS

FIG. 1 shows the C-terminal 36 amino acid sequence of the Cellulase and the linkage sites of the disulfide bonds.

FIG. 2 shows a 587-bp DNA fragment (SEQ. No.1) consisting of a T7 promoter and the sequence between the thioredoxin (TRX) coding sequence and NcoI cloning site.

FIG. 3 shows a 36-mer oligonucleotide (SEQ. NO.2), and 3B shows a 52-mer oligonucleotide (SEQ. NO.3) used as primers in PCR to amplify the DNA fragment encoding the cellulose binding domain.

FIG. 4 shows the modified DNA sequence encoding the cellulose binding domain and an RGD tripeptide.

Figure 5:
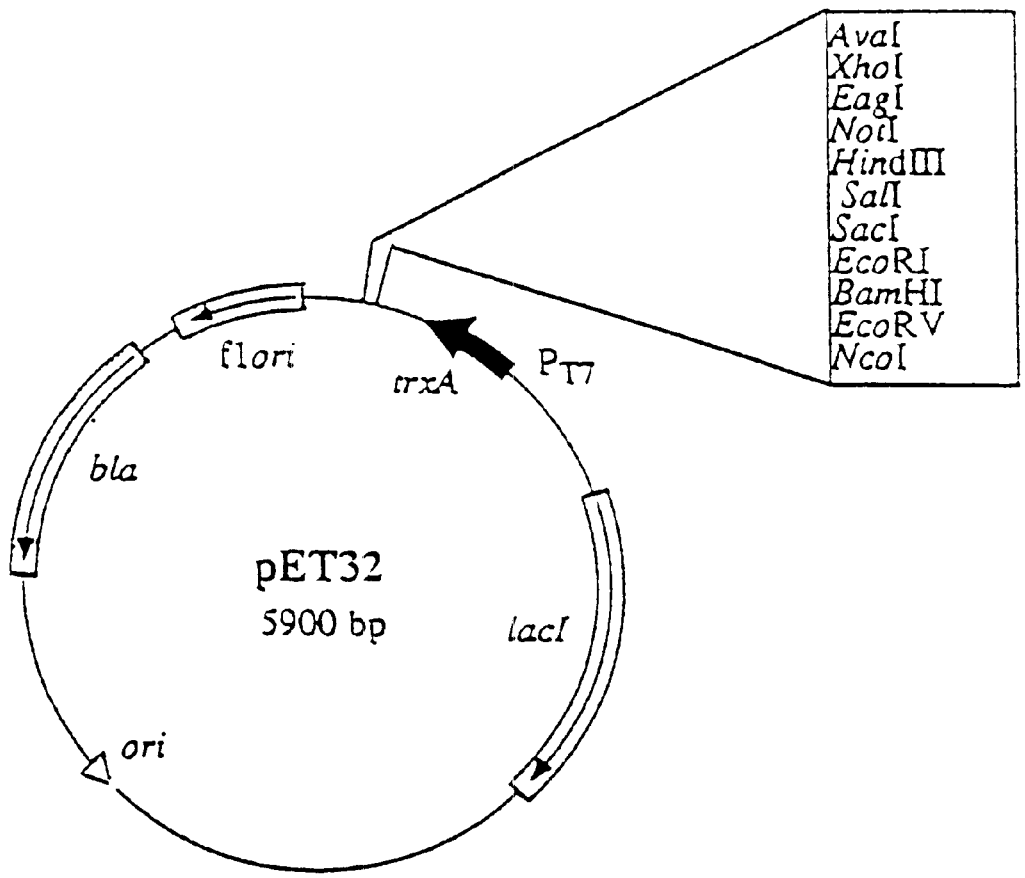

FIG. 5 shows a gene map of pET32 used to clone the DNA sequences encoding a desired chimeric protein with a cellulose binding domain, wherein the map comprises the cleavage sites of restriction enzymes, a T7 promoter, antibotic genes and relative orientations.

Figure 6:
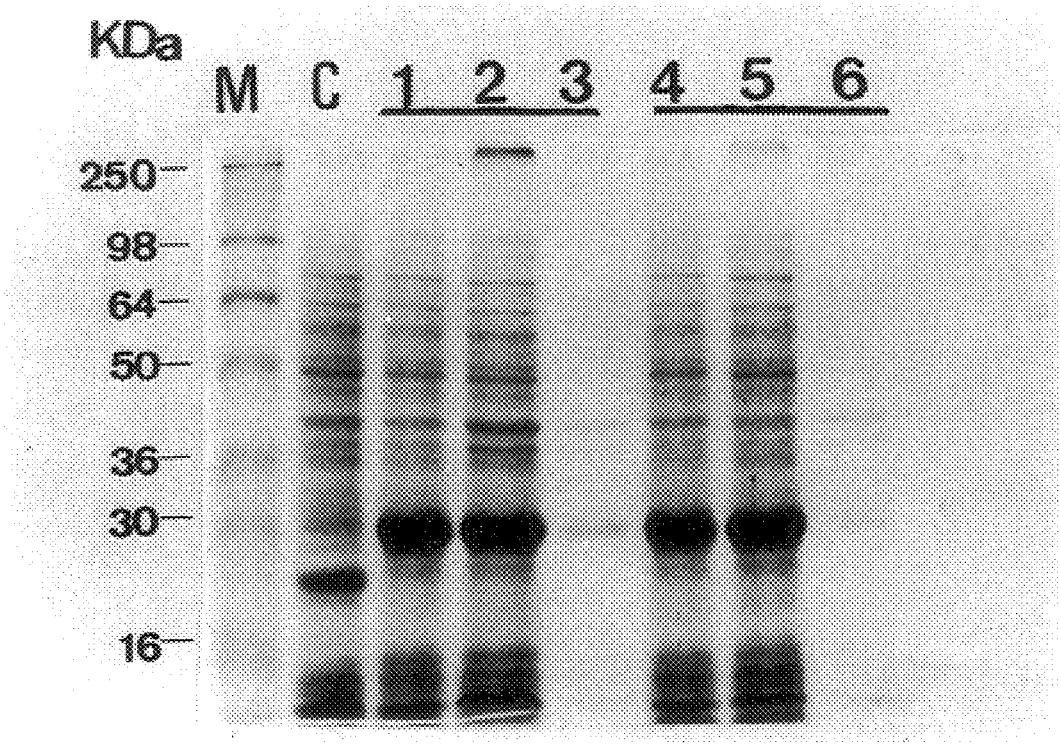

FIG. 6 depicts the distribution of the chimeric protein (TRX-CBD-RGD) in *E. coli*.

Figure 7:
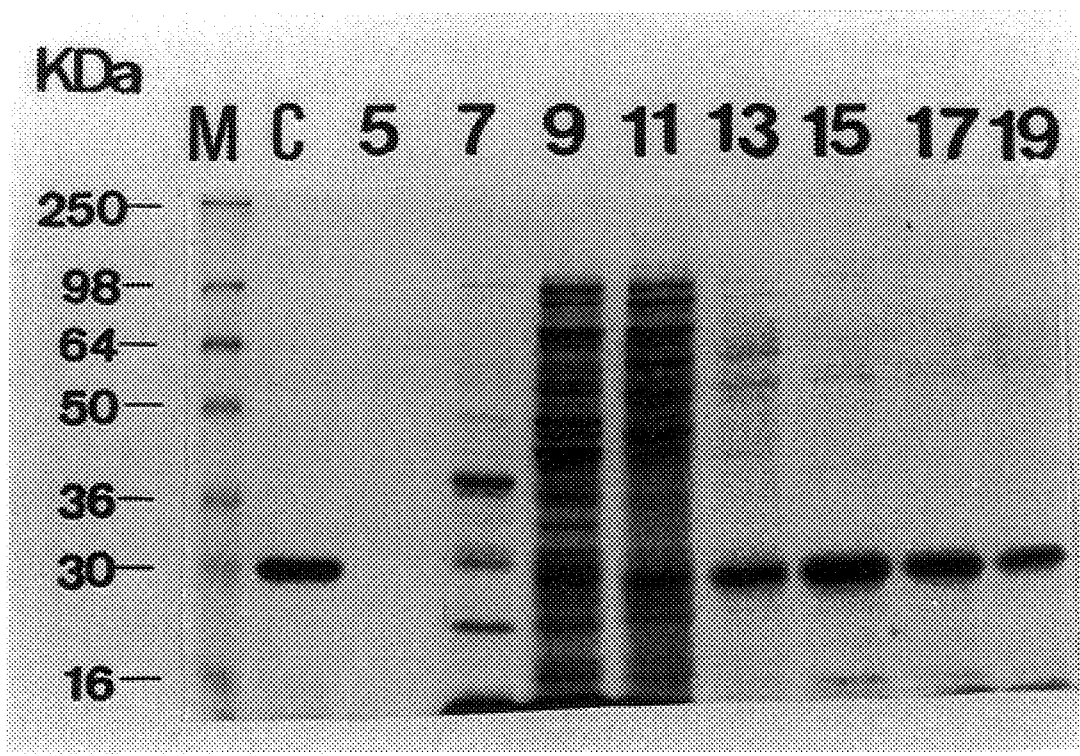

FIG. 7 is a SDS-PAGE showing the chimeric proteins collected from an anion-exchange resin column.

FIGS. 8A–8C are pictures showing the attachment results of Mardin-Darby bovine kidney cells (MDBK: $5\times10^5$ cells) plated in culture plates coated without (FIG. 8A) or with (FIGS. 8B, 8C) the chimeric proteins, wherein the plate in FIG. 8B is coated with a non-CBD-RGD protein, and the plate in FIG. 8C is coated with a chimeric protein: TRX-CBD-RGD.

DETAILED DESCRIPTION OF THE INVENTION

One feature of this invention is to provide a chimeric protein, comprising a cellulose binding domain (CBD) and two polypeptide sequences with independent functions (i.e., two independent desired proteins) joined at the C-terminal and N-terminal of the cellulose binding domain. The independent desired proteins include Protein A, Protein G, streptavidin, avidin, Taq polymerase, non-Taq polymerase, alkaline phosphatase, RNase, DNase, restriction enzymes, peroxidases, glucanases, chitinases, beta and alpha glucosidases, beta and alpha glucoronidase, amylases, transferases, beta-lactamase, non-beta lactamase antibiotic modifying and degrading enzymes, luciferase, esterases, lipases, proteases, bacteriocins, antibiotics, enzyme inhibitors, growth factors, hormones, receptors, antigens, membrane proteins, nuclear proteins, transcriptional and translational factors and nucleic acid modifying enzymes. The preferrable ones are thioredoxin, and an Arginine-Glutamate-Asparate (RGD) tripeptide.

The CBD applied in this invention can be generated from the cellulobiohydrolase I of *Trichoderma konigii* G39 (CCRC 930014; isolated by the inventors) or modified cellulobiohydrolase I of *Trichoderma konigii* G39 (cellulobiohydrolase I, CBH I), which is composed of 513 amino acid. The amino acid sequences of the two cellulases isolated from *Trichoderma konigii* G39 (cellulobiohydrolase I, CBH I) and *Trichoderma reesei* are identical.

The structure of the cellulase can be divided into an N-terminal catalytic domain and a C-terminal CBD composed of 36 amino acid residues. These two distinct functional domains are linked together by a 30-mer peptide composed of proline-rich and threonine-rich amino acid to form a complete cellulase. The NMR analysis shows that the C-terminal which is composed of 36 amino acid residues can fold into a stable 3-D structure by two disulfide bonds, and the tertiary structure can independently bind to cellulose. The specific linking sites of the disulfide bonds within the C-terminal composed of 36 amino acid residues are shown in FIG. 1. The binding affinity between the chimeric protein and the cellulose can be enhanced by replacing the code encoding the fifth amino acid residue of the binding domain from tyrosine to tryptophan.

As described above, the chimeric protein composed of a desired protein and a binding domain obtained from the N-terminal of the cellulase from *Cellulomonas fimi* bacteria still has the cellulose binding ability. The chimeric protein containing a cellulose binding domain can be applied to purify desired recombinant proteins.

Another feature of this invention is to provide transformed cells comprising the recombinant expression vector as described above, wherein the cells used for transformation can be either prokaryotes or eukaryotes. The preferable prokaryote used for this purpose is *E. coli*. For example, a transformed prokaryote produced according to this invention is obtained by transforming a vector, pETC/R, containing the coding sequence of a chimeric protein with a cellulose binding domain to *E. coli* BL21 (DE3) to produce a pETC/R transformed *E. coli* BL21 (DE3) (CCRC 940176). The cellulose binding domain coding sequence can be isolated from *Trichoderma konigii* G39 (CCRC 930014; isolated by the inventors).

Embodiment

In order to generate a chimeric protein with the function of enhancing cells attachment to a matrix coated with cellulose, a polypeptide comprising a cellulose binding domain is provided. The N-terminal of the polypeptide comprising a cellulose binding domain is joined to a thioredoxin, and the C-terminal of the polypeptide is joined to an Arginine-Glutamate-Asparate (RGD) tripeptide, which is the smallest functional unit useful in promoting the attachment of animal cells onto the cell walls of plants. Subsequently, the sequence encoding the polypeptide is cloned into an expression vector, such as *E. coli* expression vector pET32 (FIG. 5), wherein the insert is situated downstream of a strong T7 promoter of a bacteriophage and the thioredoxin sequence is adjacent to a T7 promoter. The relative sites of the T7 promoter, the thioredoxin amino acid sequence and the NcoI cloning site are listed in FIG. 2.

In order to generate a DNA sequence encoding a cellulose binding domain and an RGD tripeptide shown in SEQ 4, two oligonucleotides (SEQ. 2 and SEQ.3) used as primers were produced by an auto-synthesizer. The desired amplified DNA sequence encoding a cellulose binding domain and an RGD tripeptide shown in FIG. 4 can be generated by PCR, wherein a pUCC1 comprising a sequence encoding the cellulase from *Trichonderma konigii* G39 (CCRC 930014; isolated by the inventors) was added as a template of PCR in addition to the synthesized oligonucleotides and essential components for PCR. The PCR reaction mixture contains, in addition to 1 µl of pUCC1 and 1 µl of each of the two oligonucleotides (100 ng/µl/each oligonucleotide), 2 µl of PCR buffer (10 mM Tris-HCl (pH 8.8), 1.5 mM $MgCl_2$, 50 mM KCl, and 0.1% Triton X-100), 2 µl of mixture of dATP, dCTP, dGTP, and dTTP (each at 100 mM), 2 µl of DMSO, and 10.5 µl of deionized water. Then the mixture was heated to 90° C. by a thermocycler for 5 minutes to denature the double strand templates before 0.5 µl of DyNAzyme™ II DNA polymerase (at 0.2 U/µl, a product of Finnzymes Oy) was added to initiate the polymerase chain reaction. Subsequently, 0.5 µl of DyNAzyme™ II DNA polymerase was added into the heated reaction mixture to initiate the chain reaction for 30 cycles. The condition of each cycle is: (1) denaturation at 94° C. for 1 minute; (2) annealing at 50° C. for 1 minute; and (3) elongation at 72° C. for 30 seconds. The PCR product generated according to above protocols is a DNA fragment with a length of 158 base pairs encoding the cellulose binding domain and an RGD tripeptide.

Next, the DNA fragment encoding the cellulose binding domain and RGD amino acid sequence generated from PCR was cleaved by NcoI before being cloned into pET32 (shown as FIG. 5), which has been cleaved with NcoI and EcoRV. The ligation reaction mixture was then transformed into *E. coli* DH5α and selected on Luria-Bertain agar plate (Bacto-tryptone 10 g, Bacto-yeast extract 5 g, NaCl 10 g, Bacto-agar 15 g per liter) containing 20 µg/ml ampicillin. The correct plasmid was identified upon NheI digestion and confirmed with DNA sequencing results. The correct plasmid was designated as pETC/R and transformed into *E. coli* BL21 (DE3) to produce a pETC/R transformed *E. coli* BL21 (DE3) (CCRC 940176). for protein production.

In order to obtain a chimeric protein (i.e., TRX-CBD-RGD) *E. coli*. BL21 (DE3) transformed with the recombinant pETC/R vector to overexpress the chimeric protein cloned in pETC/R vector. The transformed *E. coli*. BL21 (DE3) cells (CCRC 940176) were further cultured by shaking in a culture medium containing ampicillin (50 µg/ml) in an incubator at 37° C. until log phase.

The chimeric proteins were further collected from *E. coli* after an inducer, IPTG (isopropyl β D-thiogalactopyranoside, 1 mM), was added and post incubated for 3 hours. The total water-soluble proteins were collected after the cells were lysed by traditional lysis buffer, wherein the content of the chimeric protein reached half of the total water-soluble proteins.

The total water-soluble proteins collected from two independent transformed *E. coli* BL21 (DE3) were electrophoresed in 12% SDS-PAGE. The stained SDS-PAGE is shown in FIG. 6, wherein symbol M indicates protein markers; C indicates the control total protein sample isolated from the *E.coli*. transformed with pET32; samples 1~3 indicate the protein sample isolated from the *E.coli*. BL21 (DE3) transformed with pETC/R containing a TRX-CBD-RGD coding sequence; samples 4~6 indicate the protein sample isolated from another *E.coli*. BL21 (DE3) transformed with pETC/R containing a TRX-CBD-RGD coding sequence; sample 1 and 4 comprise the total proteins, sample 2 and 5 comprise water-soluble proteins, samples 3 and 6 comprise water-insoluble proteins.

The total water soluble proteins from transformed *E. coli* BL21 (DE3) were further purified through an ion-exchange liquid chromatography, such as an anion-exchange resin DE52 column, and a purified chimeric protein (TRX-CBD-RGD) with a purity no less than 99% was generated. Moreover, the purified proteins collected from the eluate of the ion-exchange liquid chromatography were further electrophoresed in an SDS-PAGE. The stained SDS-PAGE is shown in FIG. 7, wherein symbol M indicates the protein markers with known molecule weight; C indicates the purified chimeric protein (TRX-CBD-RGD) with a molecular weight of 30 KDa; No. 5, 7, 9, 11, 13, 15, 17, 19 indicate the protein samples collected from 5, 7, 9, 11, 13, 15, 17, 19 eluate of the anion-exchange column. As shown in FIG. 7, eluate 11, 13, 15, 17, and 19 contain the chimeric protein with a purity greater than 99%. The purified chimeric protein (TRX-CBD-RGD) has the ability to promote cell attachment onto the matrix coated with cellulose.

The acetic cellulose was dissolved in a 2% acetic aqueous solution to produce a saturated acetic cellulose solution. Then 400 µl of the saturated acetic cellulose solution was directed to each well of 24-well microplates and allowed to dry in air. After the 24-well microplates were washed once with PBS, the acetic cellulose coated plates were generated. Next, a sufficient amount of the chimeric protein of chimeric protein in Tris-HCl buffered solution (pH 7.4)) was directed to each well and incubated at room temperature for 2~4 hours. After the Tris-HCl buffered solution was removed from the plates and washing 2~3 times with serum free DMEM medium (Dulbecco's modified Eagle medium), Mardin-Darby bovine kidney (MDBX) cells were subsequently plated on each well of the 24-well microplates in a concentration of 5×10⁵ cells per well and incubated in an incubator at 37° C. for 3 hours. As shown in FIG. 8C, the attachment of the cells plated on the plate coated with the purified chimeric protein were obvious. However the cells incubated in the plate not coated with the purified chimeric protein were all of circular shape with (FIG. 8A) or without (FIG. 8B) any extra protein having been added, which indicates that the cells shown in FIGS. 8A and 8B did not attach to the wells of the 24-well microplates.

Moreover, the numbers of cells suspended in the culture medium were counted 3 hours after the cells were plated on chimeric protein coated plates. The result shows that the number of unattached cells was less than 5% of total cells.

It is to be understood that while the invention has been described in conjunction with the detailed description thereof, that the foregoing description is intended to illustrate and not limit the scope of the invention, which is defined by the scope of the appended claims. Other aspects, advantages, and modifications are within the scope of the following claims.

What is claimed:

1. A chimeric protein comprising a cellulose-binding domain (CBD) having a C-terminal site and an N-terminal site, wherein said C-terminal site of said CBD is joined to a peptide containing arginine-glutamate-aspartate (RGD), and wherein said N-terminal site of said CBD is joined to a thioredoxin (TRX);
   wherein said CBD comprises the amino acid sequence of SEQ ID NO: 5 and wherein said TRX comprises the amino acid sequence of SEQ ID NO: 10.

2. A chimeric protein comprising a cellulose-binding domain (CBD) having a C-terminal site and an N-terminal site, wherein said C-terminal site of said CBD is joined to a peptide containing arginine-glutamate-aspartate (RGD), and wherein said N-terminal site of said CBD is joined to a thioredoxin (TRX);
   wherein said CBD comprises the amino acid sequence of SEQ ID NO: 5 in which the fifth amino acid residue of SEQ ID NO:5 is changed from tyrosine to tryptophan; and
   wherein said TRX comprises the amino acid sequence of SEQ ID NO: 10.

3. A chimeric protein comprising a cellulose-binding domain (CBD), wherein said chimeric protein has the amino acid sequence of SEQ ID NO:11.

* * * * *

SEQUENCE LISTING

<160> NUMBER OF SEQ ID NOS: 11

<210> SEQ ID NO 1
<211> LENGTH: 587
<212> TYPE: DNA
<213> ORGANISM: Unknown
<220> FEATURE:
<221> NAME/KEY: thioredoxin
<222> LOCATION: 89..415
<223> OTHER INFORMATION: Combined DNA of thiore doxin and artificial
      sequence

<400> SEQUENCE: 1

```
taatacgact cactataggg gaattgtgag cggataacaa ttcccctcta g aaataattt      60 tgtttaactt taagaaggag atatacat atg agc gat aaa att  att cac ctg      112
                                Met Ser Asp Lys Ile Ile His Leu
                                 1               5 act gac gac agt ttt gac acg gat gta ctc a aa gcg gac ggg gcg atc      160
Thr Asp Asp Ser Phe Asp Thr Asp Val leu L ys Ala Asp Gly Ala Ile
    10                  15                  20 ctc gtc gat ttc tgg gca gag tgg tgc ggt c cg tgc aaa atg atc gcc      208
Leu Val Asp Phe Trp Ala Glu Trp Cys Gly P ro Cys Lys Met Ile Ala
25                  30                  35                  40 ccg att ctg gat gaa atc gct gac gaa tat c ag ggc aaa ctg acc gtt      256
Pro Ile Leu Asp Glu Ile Ala Asp Glu Tyr G ln Gly Lys Leu Thr Val
                45                  50                  55 gca aaa ctg aac atc gat caa aac cct ggc a ct gcg ccg aaa tat ggc      304
Ala Lys Leu Asn Ile Asp Gln Asn Pro Gly T hr Ala Pro Lys Tyr Gly
            60                  65                  70 atc cgt ggt atc ccg act ctg ctg ctg ttc a aa aac ggt gaa gtg gcg      352
Ile Arg Gly Ile pro Thr Leu Leu leu Phe L ys Asn Gly Glu Val Ala
        75                  80                  85 gca acc aaa gtg ggt gca ctg tct aaa ggt c ag ttg aaa gag ttc ctc      400
Ala Thr Lys Val Gly Ala Leu Ser Lys Gly G ln Leu Lys Glu Phe Leu
    90                  95                  100 gac gct aac ctg gcc ggttctggtt ctggccatat gcaccatc at catcatcatt      455
Leu Ala Asn Leu Ala
105 cttctggtct ggtgccacgc ggttctggta tgaaagaaac cgctgctgct a aattcgaac      515 gccagcacat ggacagccca gatctgggta ccgatgacga cgacaagagc c cgggcttct      575 cctcaaccat gg                                                          587
```

<210> SEQ ID NO 2
<211> LENGTH: 36
<212> TYPE: DNA
<213> ORGANISM: Artificial Sequence
<220> FEATURE:

<223> OTHER INFORMATION: Primer

<400> SEQUENCE: 2
cttccatggc tacccagtct cactggggcc agtgcg                              36

<210> SEQ ID NO 3
<211> LENGTH: 49
<212> TYPE: DNA
<213> ORGANISM: Artificial Sequence
<220> FEATURE:
<223> OTHER INFORMATION: Primer

<400> SEQUENCE: 3 tca gct agc gct gtc acc acg acc agt tgg a gt agt tgg cag gca ctg    48 a                                                                    49

<210> SEQ ID NO 4
<211> LENGTH: 158
<212> TYPE: DNA
<213> ORGANISM: Unknown
<220> FEATURE:
<221> NAME/KEY: Cellulose binding domain
<222> LOCATION: 12..119
<221> NAME/KEY: RGD
<222> LOCATION: 138..146
<223> OTHER INFORMATION: Combined DNA of artifi cial sequence, cellulose
      binding domain, and artificial sequ ence

<400> SEQUENCE: 4 cttcc atg gct acc cag tct cac tac ggc cag tgc ggc ggt att gcc tac    50
      Met Ala Thr Gln Ser His Tyr Gly Gln Cys Gly Gly Ile Gly Tyr
        1               5                  10                  15 agc ggc ccc acg gtc tgc gcc agc ggc aca a ct tgc cag gtc ctg aac    98
Ser Gly Pro Thr Val Cys Ala Ser Gly Thr T hr Cys Gln Val Leu Asn
             20                  25                  30 cct tac tac tct cag tgc ctg cca act act c ca act ggt cgt ggt gac    146
Pro Tyr Tyr Ser Gln Cys Leu Pro Thr Thr P ro Thr Gly Arg Gly Asp
         35                  40                  45 agc gct agc tga                                                      158
Ser Ala Ser
        50

<210> SEQ ID NO 5
<211> LENGTH: 36
<212> TYPE: PRT
<213> ORGANISM: Trichoderma konigii

<400> SEQUENCE: 5

Thr Gln Ser His Tyr Gly Gln Cys Gly Gly I le Gly Tyr Ser Gly Pro
  1               5                  10                  15

Thr Val Cys Ala Ser Gly Thr Thr Cys Gln V al Leu Asn Pro Tyr Tyr
             20                  25                  30

Ser Gln Cys Leu
         35  36

<210> SEQ ID NO 6
<211> LENGTH: 327
<212> TYPE: DNA
<213> ORGANISM: Unknown
<220> FEATURE:
<221> NAME/KEY: thioredoxin
<222> LOCATION: 1..327
<223> OTHER INFORMATION: DNA sequence of thiore doxin

<400> SEQUENCE: 6

```
atg agc gat aaa att att cac ctg act gac g ac agt ttt gac acg gat    48
Met Ser Asp Lys Ile Ile His Leu Thr Asp A sp Ser Phe Asp Thr Asp
1               5                   10                  15 gta ctc aaa gcg gac ggg gcg atc ctc gtc g at ttc tgg gca gag tgg    96
Val leu Lys Ala Asp Gly Ala Ile Leu Val A sp Phe Trp Ala Glu Trp
                20                  25                  30 tgc ggt ccg tgc aaa atg atc gcc ccg att c tg gat gaa atc gct gac   144
Cys Gly Pro Cys Lys Met Ile Ala Pro Ile L eu Asp Glu Ile Ala Asp
            35                  40                  45 gaa tat cag ggc aaa ctg acc gtt gca aaa c tg aac atc gat caa aac   192
Glu Tyr Gln Gly Lys Leu Thr Val Ala Lys L eu Asn Ile Asp Gln Asn
        50                  55                  60 cct ggc act gcg ccg aaa tat ggc atc cgt g gt atc ccg act ctg ctg   240
Pro Gly Thr Ala Pro Lys Tyr Gly Ile Arg G ly Ile Pro Thr Leu Leu
65                  70                  75                  80 ctg ttc aaa aac ggt gaa gtg gcg gca acc a aa gtg ggt gca ctg tct   288
leu Phe Lys Asn Gly Glu Val Ala Ala Thr L ys Val Gly Ala Leu Ser
                85                  90                  95 aaa ggt cag ttg aaa gag ttc ctc gac gct a ac ctg gcc                327
Lys Gly Gln Leu Lys Glu Phe Leu Asp Ala A sn Leu Ala
                100                 105
```

<210> SEQ ID NO 7
<211> LENGTH: 108
<212> TYPE: DNA
<213> ORGANISM: Trichoderma konigii

<400> SEQUENCE: 7

```
cc cag tct cac tac ggc cag tgc ggc ggt at t gcc tac agc ggc ccc     48
Thr Gln Ser His Tyr Gly Gln Cys Gly Gly I le Gly Tyr Ser Gly Pro
1               5                   10                  15 acg gtc tgc gcc agc ggc aca act tgc cag g tc ctg aac cct tac tac    96
Thr Val Cys Ala Ser Gly Thr Thr Cys Gln V al Leu Asn Pro Tyr Tyr
                20                  25                  30 tct cag tgc ctg                                                    108
Ser Gln Cys Leu
        35  36
```

<210> SEQ ID NO 8
<211> LENGTH: 159
<212> TYPE: PRT
<213> ORGANISM: Unknown
<220> FEATURE:
<221> NAME/KEY: thioredoxin
<222> LOCATION: 1..109
<223> OTHER INFORMATION: Combined amino acid of thioredoxin and an
      artificial sequence

<400> SEQUENCE: 8

```
Met Ser Asp Lys Ile Ile His Leu Thr Asp A sp Ser Phe Asp Thr Asp
1               5                   10                  15

Val Leu Lys Ala Asp Gly Ala Ile Leu Val A sp Phe Trp Ala Glu Trp
                20                  25                  30

Cys Gly Pro Cys Lys Met Ile Ala Pro Ile L eu Asp Glu Ile Ala Asp
            35                  40                  45

Glu Tyr Gln Gly Lys Leu Thr Val Ala Lys L eu Asn Ile Asp Gln Asn
        50                  55                  60

Pro Gly Thr Ala Pro Lys Tyr Gly Ile Arg G ly Ile pro Thr Leu Leu
65                  70                  75                  80 leu Phe Lys Asn Gly Glu Val Ala Ala Thr L ys Val Gly Ala Leu Ser
                85                  90                  95

Lys Gly Gln Leu Lys Glu Phe Leu Asp Ala A sn Leu Ala Gly Ser Gly
                100                 105                 110
```

```
Ser Gly His Met His His His His His Ser Gly Leu Val Pro
        115             120             125

Arg Gly Ser Gly Met Leu Glu Thr Ala Ala Ala Lys Phe Glu Arg Gln
    130             135             140

His Met Asp Ser Pro Asp Leu Gly Thr Asp Asp Asp Lys Ser
145             150             155
```

<210> SEQ ID NO 9
<211> LENGTH: 44
<212> TYPE: PRT
<213> ORGANISM: Unknown
<220> FEATURE:
<221> NAME/KEY: Cellulose binding domain
<222> LOCATION: 3..38
<223> OTHER INFORMATION: Combined amino acid sequence of cellulose
      binding domain and artificial sequences

<400> SEQUENCE: 9

```
Met Ala Thr Gln Ser His Trp Gly Gln Cys Gly Gly Ile Gly Tyr Ser
1               5                   10                  15

Gly Pro Thr Val Cys Ala Ser Gly Thr Thr Cys Gln Val Leu Asn Pro
            20                  25                  30

Tyr Tyr Ser Gln Cys Leu Pro Thr Thr Pro Thr Gly
        35                  40
```

<210> SEQ ID NO 10
<211> LENGTH: 109
<212> TYPE: PRT
<213> ORGANISM: Unknown
<220> FEATURE:
<221> NAME/KEY: thioredoxin
<222> LOCATION: 1..109
<223> OTHER INFORMATION: amino acid of thioredoxin

<400> SEQUENCE: 10

```
Met Ser Asp Lys Ile Ile His Leu Thr Asp Ser Phe Asp Thr Asp
1               5                   10                  15

Val leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80 leu Phe Lys Asn Gly Glu Val Ala Ala Thr Lys Val Gly Ala Leu Ser
            85                  90                  95

Lys Gly Gln Leu Lys Glu Phe Leu Leu Ala Asn Leu Ala
                100                 105
```

<210> SEQ ID NO 11
<211> LENGTH: 209
<212> TYPE: PRT
<213> ORGANISM: Unknown
<220> FEATURE:
<221> NAME/KEY: thioredoxin
<222> LOCATION: 1..109
<221> NAME/KEY: Cellose-binding domain
<222> LOCATION: 162..197
<221> NAME/KEY: RGD
<222> LOCATION: 204..206
<223> OTHER INFORMATION: Combined amino acid sequence of thioredoxin,
      artificial sequence, cellulose-binding domain, and artificial
      sequence; the two artificial sequences flanking the

```
                cellulose-binding domain contain restriction sites

<400> SEQUENCE: 11

Met Ser Asp Lys Ile Ile His Leu Thr Asp A sp Ser Phe Asp Thr Asp
1               5                   10                  15

Val Leu Lys Ala Asp Gly Ala Ile Leu Val A sp Phe Trp Ala Glu Trp
                20              25                  30

Cys Gly Pro Cys Lys Met Ile Ala Pro Ile L eu Asp Glu Ile Ala Asp
            35              40                  45

Glu Tyr Gln Gly Lys Leu Thr Val Ala Lys L eu Asn Ile Asp Gln Asn
        50              55                  60

Pro Gly Thr Ala Pro Lys Tyr Gly Ile Arg G ly Ile Pro Thr Leu Leu
65              70              75                      80 leu Phe Lys Asn Gly Glu Val Ala Ala Thr L ys Val Gly Ala Leu Ser
                85              90                      95

Lys Gly Gln Leu Lys Glu Phe Leu Leu Ala A sn Leu Ala Gly Ser Gly
            100             105                 110

Ser Gly His Met His His His His His S er Ser Gly Leu Val Pro
            115             120             125

Arg Gly Ser Gly Met Leu Glu Thr Ala Ala A la Lys Phe Glu Arg Gln
        130             135                 140

His Met Asp Ser Pro Asp Leu Gly Thr Asp A sp Asp Asp Lys Ala Met
145             150             155                     160

Ala Thr Gln Ser His Trp Gly Gln Cys Gly G ly Ile Gly Tyr Ser Gly
                165             170                 175

Pro Thr Val Cys Ala Ser Gly Thr Thr Cys G ln Val Leu Asn Pro Tyr
            180             185                 190

Tyr Ser Gln Cys Leu Pro Thr Thr Pro Thr G ly Arg Gly Asp Ser Ala
        195             200             205

Ser
209
```